United States Patent
Braselmann

(10) Patent No.: US 6,762,284 B1
(45) Date of Patent: Jul. 13, 2004

(54) NUCLEOTIDE SEQUENCES THAT ENCODE PHOSPHATIDYLINOSITOL-3' KINASE ASSOCIATED PROTEINS AND USES THEREOF

(75) Inventor: Sylvia Braselmann, San Francisco, CA (US)

(73) Assignee: Onyx Pharmaceuticals, Inc., Richmond, CA (US)

( * ) Notice: Subject to any disclaimer, the term of this patent is extended or adjusted under 35 U.S.C. 154(b) by 0 days.

(21) Appl. No.: 09/687,230

(22) Filed: Oct. 13, 2000

Related U.S. Application Data

(62) Division of application No. 08/942,008, filed on Oct. 1, 1997, now Pat. No. 6,133,419.
(60) Provisional application No. 60/030,103, filed on Nov. 1, 1996.

(51) Int. Cl.[7] .................. C07K 17/00; C07H 21/04; C12Q 1/48; C12N 9/12
(52) U.S. Cl. .................. 530/350; 536/23.1; 435/15; 435/194
(58) Field of Search .................. 530/350; 536/23.1; 435/15, 194

(56) References Cited

PUBLICATIONS

Bork, Genome Research, 10:398–400, 2000.*
Broun et al., Science 282:1315–1317, 1998.*
Van de Loo et al., Proc. Natl. Acad. Sci. 92:6743–6747, 1995.*
Seffernick et al., J. Bacteriol. 183(8):2405–2410, 2001.*
Witkowski et al., Biochemistry 38:11643–11650, 1999.*
Felder, S. et al., Mol. Cell. Biol., vol. 13, No. 3, pp. 1449–1455, Mar. 1993.*

* cited by examiner

*Primary Examiner*—Rebecca E. Prouty
*Assistant Examiner*—Delia Ramirez
(74) *Attorney, Agent, or Firm*—Gregory Giotta

(57) ABSTRACT

Identification, characterization and expression of nucleotides that encode phosphatidylinositol-3'kinase associated protein(s) that bind to the intermediate SH2 domain on the regulatory subunit of PI3K, p85, by the associated protein(s) C-terminal amino acids, and that exhibit a bromodomain are described, as well as methods of using such proteins for medical applications, including diagnosis and treatment cell growth disorders.

3 Claims, No Drawings

SEQUENCE LISTING

<160> NUMBER OF SEQ ID NOS: 3

<210> SEQ ID NO 1
<211> LENGTH: 2307
<212> TYPE: DNA
<213> ORGANISM: Phosphatidylinositol-3' Kinase
<220> FEATURE:
<221> NAME/KEY: CDS
<222> LOCATION: (162)..(1928)
<223> OTHER INFORMATION:

<400> SEQUENCE: 1

```
ctcgaggggc atcgcgccgc cggcgcgcg ccgcccccct gcctcgcggc gcggggtctc      60 gcgggcccg ctcccgccct ccgctcgcct ggcccggacc ggaagcggcg ccgcacggcc     120
tgggcctggc gcggggggcg ggcaccgggg cccgtcgga c atg ggc aag aag cac     176
                                             Met Gly Lys Lys His
                                              1               5 aag aag cac aag tcg gac aaa cac ctc tac gag gag tat gta gag aag     224
Lys Lys His Lys Ser Asp Lys His Leu Tyr Glu Glu Tyr Val Glu Lys
             10                  15                  20 ccc ttg aag ctg gtc ctc aaa gta gga ggg aac gaa gtc acc gaa ctc     272
Pro Leu Lys Leu Val Leu Lys Val Gly Gly Asn Glu Val Thr Glu Leu
         25                  30                  35 tcc acg ggc agc tcg ggg cac gac tcc agc ctc ttc gaa gac aaa aac     320
Ser Thr Gly Ser Ser Gly His Asp Ser Ser Leu Phe Glu Asp Lys Asn
     40                  45                  50 gat cat gac aaa cac aag gac aga aag cgg aaa aag aga aag aaa gga     368
Asp His Asp Lys His Lys Asp Arg Lys Arg Lys Lys Arg Lys Lys Gly
 55                  60                  65 gag aag cag att cca ggg gaa gaa aag ggg aga aaa cgg aga aga gtt     416
Glu Lys Gln Ile Pro Gly Glu Glu Lys Gly Arg Lys Arg Arg Arg Val
 70                  75                  80                  85 aag gag gat aaa aag aag cga gat cga gac cgg gtg gag aat gag gca     464
Lys Glu Asp Lys Lys Lys Arg Asp Arg Asp Arg Val Glu Asn Glu Ala
             90                  95                 100 gaa aaa gat ctc cag tgt cac gcc cct gtg aga tta gac ttg cct cct     512
Glu Lys Asp Leu Gln Cys His Ala Pro Val Arg Leu Asp Leu Pro Pro
            105                 110                 115 gag aag cct ctc aca agc tct tta gcc aaa caa gaa gaa gta gaa cag     560
Glu Lys Pro Leu Thr Ser Ser Leu Ala Lys Gln Glu Glu Val Glu Gln
        120                 125                 130 aca ccc ctt caa gaa gct ttg aat caa ctg atg aga caa ttg cag aga     608
Thr Pro Leu Gln Glu Ala Leu Asn Gln Leu Met Arg Gln Leu Gln Arg
    135                 140                 145 aaa gat cca agt gct ttc ttt tca ttt cct gtg act gat ttt att gct     656
Lys Asp Pro Ser Ala Phe Phe Ser Phe Pro Val Thr Asp Phe Ile Ala
150                 155                 160                 165 cct ggc tac tcc atg atc att aaa cac cca atg gat ttt agt acc atg     704
Pro Gly Tyr Ser Met Ile Ile Lys His Pro Met Asp Phe Ser Thr Met
                170                 175                 180 aaa gaa aag atc aag aac aat gac tat cag tcc ata gaa gaa cta aag     752
Lys Glu Lys Ile Lys Asn Asn Asp Tyr Gln Ser Ile Glu Glu Leu Lys
            185                 190                 195 gat aac ttc aaa cta atg tgt act aat gcc atg att tac aat aaa cca     800
Asp Asn Phe Lys Leu Met Cys Thr Asn Ala Met Ile Tyr Asn Lys Pro
        200                 205                 210 gag acc att tat tat aaa gct gca aag aag ctg ttg cac tca gga atg     848
Glu Thr Ile Tyr Tyr Lys Ala Ala Lys Lys Leu Leu His Ser Gly Met
    215                 220                 225
```

-continued

```
aaa att ctt agc cag gaa aga att cag agc ctg aag cag agc ata gac        896
Lys Ile Leu Ser Gln Glu Arg Ile Gln Ser Leu Lys Gln Ser Ile Asp
230                 235                 240                 245 ttc atg gct gac ttg cag aaa act cga aag cag aaa gat gga aca gac        944
Phe Met Ala Asp Leu Gln Lys Thr Arg Lys Gln Lys Asp Gly Thr Asp
            250                 255                 260 acc tca cag agt ggg gag gac gga ggc tgc tgg cag aga gag aga gag        992
Thr Ser Gln Ser Gly Glu Asp Gly Gly Cys Trp Gln Arg Glu Arg Glu
265                 270                 275 gac tct gga gat gcc gaa gca cac gcc ttc aag agt ccc agc aaa gaa       1040
Asp Ser Gly Asp Ala Glu Ala His Ala Phe Lys Ser Pro Ser Lys Glu
    280                 285                 290 aat aaa aag aaa gac aaa gat atg ctt gaa gat aag ttt aaa agc aat       1088
Asn Lys Lys Lys Asp Lys Asp Met Leu Glu Asp Lys Phe Lys Ser Asn
295                 300                 305 aat tta gag aga gag cag gag cag ctt gac cgc atc gtg aag gaa tct       1136
Asn Leu Glu Arg Glu Gln Glu Gln Leu Asp Arg Ile Val Lys Glu Ser
310                 315                 320                 325 gga gga aag ctg acc agg cgg ctt gtg aac agt cag tgc gaa ttt gaa       1184
Gly Gly Lys Leu Thr Arg Arg Leu Val Asn Ser Gln Cys Glu Phe Glu
                330                 335                 340 aga aga aaa cca gat gga aca acg acg ttg gga ctt ctc cat cct gtg       1232
Arg Arg Lys Pro Asp Gly Thr Thr Thr Leu Gly Leu Leu His Pro Val
            345                 350                 355 gat ccc att gta gga gag cca ggc tac tgc ctg gtg aga ctg gga atg       1280
Asp Pro Ile Val Gly Glu Pro Gly Tyr Cys Leu Val Arg Leu Gly Met
        360                 365                 370 aca act gga aga ctt cag tct gga gtg aat act ttg cag ggg ttc aaa       1328
Thr Thr Gly Arg Leu Gln Ser Gly Val Asn Thr Leu Gln Gly Phe Lys
375                 380                 385 gag gat aaa agg aac aaa gtc act cca gtg tta tat ttg aat tat ggg       1376
Glu Asp Lys Arg Asn Lys Val Thr Pro Val Leu Tyr Leu Asn Tyr Gly
390                 395                 400                 405 ccc tac agt tct tat gca ccg cat tat gac tcc aca ttt gca aat atc       1424
Pro Tyr Ser Ser Tyr Ala Pro His Tyr Asp Ser Thr Phe Ala Asn Ile
                410                 415                 420 agc aag gat gat tct gat tta atc tat tca acc tat ggg gaa gac tct       1472
Ser Lys Asp Asp Ser Asp Leu Ile Tyr Ser Thr Tyr Gly Glu Asp Ser
            425                 430                 435 gat ctt cca agt gat ttc agc atc cat gag ttt ttg gcc acg tgc caa       1520
Asp Leu Pro Ser Asp Phe Ser Ile His Glu Phe Leu Ala Thr Cys Gln
        440                 445                 450 gat tat ccg tat gtc atg gca gat agt tta ctg gat gtt tta aca aaa       1568
Asp Tyr Pro Tyr Val Met Ala Asp Ser Leu Leu Asp Val Leu Thr Lys
455                 460                 465 gga ggg cat tcc agg acc cta caa gag atg gag atg tca ttg cct gaa       1616
Gly Gly His Ser Arg Thr Leu Gln Glu Met Glu Met Ser Leu Pro Glu
470                 475                 480                 485 gat gaa ggc cat act agg aca ctt gac aca gga aaa gaa atg gag cag       1664
Asp Glu Gly His Thr Arg Thr Leu Asp Thr Gly Lys Glu Met Glu Gln
                490                 495                 500 att aca gaa gta gag cca cca ggg cgt ttg gac tcc agt act caa gac       1712
Ile Thr Glu Val Glu Pro Pro Gly Arg Leu Asp Ser Ser Thr Gln Asp
            505                 510                 515 agg ctc ata gcg ctg aaa gca gta aca aat ttt ggc gtt cca gtt gaa       1760
Arg Leu Ile Ala Leu Lys Ala Val Thr Asn Phe Gly Val Pro Val Glu
        520                 525                 530 gtt ttt gac tct gaa gaa gct gaa ata ttc cag aag aaa ctt gat gag       1808
Val Phe Asp Ser Glu Glu Ala Glu Ile Phe Gln Lys Lys Leu Asp Glu
```

```
        535                 540                 545
acc acc aga ttg ctc agg gaa ctc cag gaa gcc cag aat gaa cgt ttg         1856
Thr Thr Arg Leu Leu Arg Glu Leu Gln Glu Ala Gln Asn Glu Arg Leu
550                 555                 560                 565 agc acc aga ccc cct ggg aac atg atc tgt ctc ttg ggt ccc tca tca         1904
Ser Thr Arg Pro Pro Gly Asn Met Ile Cys Leu Leu Gly Pro Ser Ser
                570                 575                 580 gag aaa tgc atc ttg ctg aac aag tgaccaataa tcttaaagaa ttgcacagca       1958
Glu Lys Cys Ile Leu Leu Asn Lys
                585 agtaactcca ggtgatatcg taagcacgta tggagttcga aaagcaatgg ggatttccat      2018 tccttcccccc gtcatggaaa acaactttgt ggatttgaca aagacactg aagaacctaa      2078 aaagacggat gttgatgagt gtcgacctgg tggaagttga ggctgcctgg tatttgatta      2138 tatattatgt acatactttt tcattcttaa cttagaaatg cttttcagaa gatattaaat      2198 atttgtaaat tgtgttttta attaaacttt tggaacagcg aatttggatg ttccagaggt      2258 tggacttgta ttaggtaata aagctggacc tgggactcgt gaggaagga                  2307

<210> SEQ ID NO 2
<211> LENGTH: 589
<212> TYPE: PRT
<213> ORGANISM: Phosphatidylinositol-3' Kinase

<400> SEQUENCE: 2

Met Gly Lys Lys His Lys Lys His Lys Ser Asp Lys His Leu Tyr Glu
1               5                   10                  15

Glu Tyr Val Glu Lys Pro Leu Lys Leu Val Leu Lys Val Gly Gly Asn
                20                  25                  30

Glu Val Thr Glu Leu Ser Thr Gly Ser Ser Gly His Asp Ser Ser Leu
            35                  40                  45

Phe Glu Asp Lys Asn Asp His Asp Lys His Lys Asp Arg Lys Arg Lys
        50                  55                  60

Lys Arg Lys Lys Gly Glu Lys Gln Ile Pro Gly Glu Glu Lys Gly Arg
65                  70                  75                  80

Lys Arg Arg Arg Val Lys Glu Asp Lys Lys Lys Arg Asp Arg Asp Arg
                85                  90                  95

Val Glu Asn Glu Ala Glu Lys Asp Leu Gln Cys His Ala Pro Val Arg
            100                 105                 110

Leu Asp Leu Pro Pro Glu Lys Pro Leu Thr Ser Ser Leu Ala Lys Gln
        115                 120                 125

Glu Glu Val Glu Gln Thr Pro Leu Gln Glu Ala Leu Asn Gln Leu Met
    130                 135                 140

Arg Gln Leu Gln Arg Lys Asp Pro Ser Ala Phe Phe Ser Phe Pro Val
145                 150                 155                 160

Thr Asp Phe Ile Ala Pro Gly Tyr Ser Met Ile Ile Lys His Pro Met
                165                 170                 175

Asp Phe Ser Thr Met Lys Glu Lys Ile Lys Asn Asn Asp Tyr Gln Ser
            180                 185                 190

Ile Glu Glu Leu Lys Asp Asn Phe Lys Leu Met Cys Thr Asn Ala Met
        195                 200                 205

Ile Tyr Asn Lys Pro Glu Thr Ile Tyr Tyr Lys Ala Ala Lys Lys Leu
    210                 215                 220

Leu His Ser Gly Met Lys Ile Leu Ser Gln Glu Arg Ile Gln Ser Leu
225                 230                 235                 240
```

-continued

```
Lys Gln Ser Ile Asp Phe Met Ala Asp Leu Gln Lys Thr Arg Lys Gln
                245                 250                 255

Lys Asp Gly Thr Asp Thr Ser Gln Ser Gly Glu Asp Gly Gly Cys Trp
            260                 265                 270

Gln Arg Glu Arg Glu Asp Ser Gly Asp Ala Glu Ala His Ala Phe Lys
        275                 280                 285

Ser Pro Ser Lys Glu Asn Lys Lys Asp Lys Asp Met Leu Glu Asp
    290                 295                 300

Lys Phe Lys Ser Asn Asn Leu Glu Arg Glu Gln Glu Gln Leu Asp Arg
305                 310                 315                 320

Ile Val Lys Glu Ser Gly Lys Leu Thr Arg Arg Leu Val Asn Ser
                325                 330                 335

Gln Cys Glu Phe Glu Arg Arg Lys Pro Asp Gly Thr Thr Thr Leu Gly
            340                 345                 350

Leu Leu His Pro Val Asp Pro Ile Val Gly Glu Pro Gly Tyr Cys Leu
        355                 360                 365

Val Arg Leu Gly Met Thr Thr Gly Arg Leu Gln Ser Gly Val Asn Thr
    370                 375                 380

Leu Gln Gly Phe Lys Glu Asp Lys Arg Asn Lys Val Thr Pro Val Leu
385                 390                 395                 400

Tyr Leu Asn Tyr Gly Pro Tyr Ser Ser Tyr Ala Pro His Tyr Asp Ser
                405                 410                 415

Thr Phe Ala Asn Ile Ser Lys Asp Asp Ser Asp Leu Ile Tyr Ser Thr
            420                 425                 430

Tyr Gly Glu Asp Ser Asp Leu Pro Ser Asp Phe Ser Ile His Glu Phe
        435                 440                 445

Leu Ala Thr Cys Gln Asp Tyr Pro Tyr Val Met Ala Asp Ser Leu Leu
    450                 455                 460

Asp Val Leu Thr Lys Gly Gly His Ser Arg Thr Leu Gln Glu Met Glu
465                 470                 475                 480

Met Ser Leu Pro Glu Asp Glu Gly His Thr Arg Thr Leu Asp Thr Gly
                485                 490                 495

Lys Glu Met Glu Gln Ile Thr Glu Val Glu Pro Pro Gly Arg Leu Asp
            500                 505                 510

Ser Ser Thr Gln Asp Arg Leu Ile Ala Leu Lys Ala Val Thr Asn Phe
        515                 520                 525

Gly Val Pro Val Glu Val Phe Asp Ser Glu Glu Ala Glu Ile Phe Gln
    530                 535                 540

Lys Lys Leu Asp Glu Thr Thr Arg Leu Leu Arg Glu Leu Gln Glu Ala
545                 550                 555                 560

Gln Asn Glu Arg Leu Ser Thr Arg Pro Pro Gly Asn Met Ile Cys Leu
                565                 570                 575

Leu Gly Pro Ser Ser Glu Lys Cys Ile Leu Leu Asn Lys
            580                 585
```

<210> SEQ ID NO 3
<211> LENGTH: 27
<212> TYPE: DNA
<213> ORGANISM: Artificial Sequence
<220> FEATURE:
<223> OTHER INFORMATION: PI3 Kinase associated protein (PIKAP)

<400> SEQUENCE: 3
ccggggatcc ccatggctag ccatatg    27

NUCLEOTIDE SEQUENCES THAT ENCODE PHOSPHATIDYLINOSITOL-3' KINASE ASSOCIATED PROTEINS AND USES THEREOF

This application is a divisional of U.S. Ser. No. 08/942,008, filed Oct. 1, 1997; now U.S. Pat. No. 6,133,419, issued Oct. 17, 2000; which claims priority from U.S. Ser. No. 60/030,103, filed Nov. 1, 1996.

FIELD OF THE INVENTION

The present invention is in the field of molecular biology, and particularly to cellular signal transduction involving nucleotide sequences that encode phosphatidylinositol-3'-kinase associated proteins, and uses of these proteins in the treatment and diagnosis of disease, preferably diseases causes by cell growth disorders.

BACKGROUND OF THE INVENTION

Phosphatidylinositol-3'-kinases (PI3Ks) are a large family of enzymes capable of 3-phosphorylating at least one of the cellular phosphoinositides (Whitman et al., 1988, Nature 332:644–646; Auger et al., 1989, Cell 57:167–175). 3-phosphorylated phosphoinositides are found in all higher eukaryotic cells. A growing body of evidence implicates PI3K and a lipid product of this enzyme, phosphatidylinositol (3,4,5)-triphosphate (hereinafter "PtdIns(3,4,5)$P_3$"), as part of a novel and important second messenger system in cellular signal transduction. The components of this novel PtdIns(3,4,5)$P_3$-based signaling system appear to be independent of the previously characterized signaling pathway based on inositol phospholipids, in which a phosphoinositidase C (PIC) hydrolyses PtdIns(4,5)$P_2$ to release the structurally distinct second messengers inositol (1,4,5)-triphosphate (Ins(1,4,5)$P_3$) and diacylglycerol.

Select extracellular agonists and growth factors will stimulate intracellular PI3K activity and cause the rapid and transient intracellular accumulation of PtdIns(3,4,5)$P_3$. Surprisingly, stimulation of a variety of different types of cell surface receptors, including receptor tyrosine kinases, receptors associated with src family non-receptor tyrosine kinases, cytokine growth factors, and G protein coupled receptors will all activate members of the PI3K family. (Reviewed in Stephens et al., 1993, Biochemica et Biophysica Acta, 1179:27–75). For example, tyrosine kinase receptors which, when activated, result in increased accumulation of PtdIns(3,4,5)$P_3$ are the PDGF receptor, the EGF receptor, members of the FGF receptor family, the CSF-1 receptor, the insulin receptor, the IGF-1 receptor, and the NGF receptor. Receptors associated with src family non-receptor tyrosine kinases which stimulate PtdIns(3,4,5)$P_3$ accumulation are the Il-2 receptor, Il-3 receptor, mIgM receptor, the CD4 receptor, the CD2 receptor, and the CD3/T cell receptor. Additionally, the cytokine Il-4 receptor and the G protein linked thrombin receptor, ATP receptor, and the fMLP receptor all stimulate the activity of a PI3K, resulting in subsequent PtdIns(3,4,5)$P_3$ accumulation. Thus, PtdIns(3,4,5)$P_3$ appears to be a second messenger in extremely diverse signaling pathways.

Support for the proposition that PI3K activity and production of PtdIns(3,4,5)$P_3$ is a physiological relevant pathway of signal transduction for these diverse receptors is derived, inter alia, from two different lines of experimental evidence: inhibition of PI3K activity by fungal metabolites and observations of direct protein associations. Wortmannin, a fungal metabolite, irreversibly inhibits PI3K activity by binding covalently to the catalytic domain of this enzyme. Inhibition of PI3K activity by Wortmannin eliminates the subsequent cellular response to the extracellular factor. For example, neutrophils respond to the chemokine fMet-Leu-Phe (fMLP) by stimulating PI3K and synthesizing PtdIns(3,4,5)$P_3$. The synthesis correlates with activation of the respiratory burst involved in neutrophil destruction of invading microorganisms. Treatment of neutrophils with Wortmannin prevents the fMLP-induced respiratory burst response. (Thelen et al., 1994, PNAS, USA 91:4960–4964.) Indeed, these experiments with Wortmannin, as well as other experimental evidence, shows that PI3K activity in cells of hematopoietic lineage, particularly neutrophils, monocytes, and other types of leukocytes, is involved in many of the non-memory immune responses associated with acute and chronic inflammation.

PI3K enzymes interact directly with, and may be co-purified with, activated forms of several receptor tyrosine kinases. When purified, receptor tyrosine kinase associated PI3K was found to consist of 170–200 kD heterodimers (Otsu et al., 1991, Cell 65:91–104, Pons et al., 1995, Mol. Cell. Biol. 15:4453–4465, Inukai et al., 1996, J. Biol. Chem. 271:5317–5320) comprising a catalytic subunit and an adapter (or regulatory) subunit.

Two different homologs of the catalytic subunit, p110 and p110β, have been described and cloned. The catalytic subunit, which irreversibly binds Wortmannin, tightly associates with one or other members of a small family of highly related regulatory subunits, p55, p55PIK p85α and p85β, to form the 170–200 kD heterodimers. The known regulatory subunits contain a large collection of protein:protein interaction domains, including two SH2 domains (Cantley et al., 1991, Cell 64:281–302).

The presence of the SH2 domains are thought to be responsible for the binding and stimulation of PI3K heterodimers to activated receptor tyrosine kinases. Activated receptors are phosphorylated at key tyrosine residues within local consensus sequences preferred by the SH2 domains found in the 55–87 kD PI3K adaptors (Songyang et al., 1993, Cell 72:767–778). Once the PI3K heterodimer binds, it directly activates the PI3K catalytic subunit (although this effect is relatively small in vitro, Carpenter et al., 1993, J. Biol. Chem. 268:9478–9483, Backer et al., 1992, EMBO J. 11:3469–3479) and translocates the cytosolic PI3K to a source of its phospholipid substrate. The combination of these factors leads to a surge in PtdIns(3,4,5)$P_3$ production. Clearly, these isoforms of PI3Ks seem structurally adapted to function as dedicated signal transducers downstream of receptor-regulated tyrosine kinases.

However, the p110/p85 sub-family of PI3Ks do not seem to be involved in the production of PtdIns(3,4,5)$P_3$ that can occur as a result of activation of cell surface receptors which utilize heterotrimeric GTPases to transduce their signals (e.g., fMLP, PAF, ATP, and thrombin). These types of cell surface receptors have been primarily described in cells of hematopoietic origin whose activation is involved in inflammatory responses of the immune system. Recent evidence has suggested that a chromatographically distinct form of Wortmannin-sensitive PI3K is present in U937 cells and neutrophils that possesses a native, relative molecular mass of about 220 kD (Stephens et al., 1994, Cell 77:83–93). This PI3K activity can be specifically stimulated by Gβγ subunits, but not Gα-GTP subunits. A similar PI3K activity has also been described in an osteosarcoma cell line (Morris et al., 1995, Mol. Pharm. 48:532–539). Platelets also contain a Gβγ-sensitive PI3K, although it is unclear whether this is a p85/p110 PI3K family member (Thomason et al., 1994, J.

Biol. Chem. 269:16525–16528). It seemed likely that this poorly characterized, Gβγ sensitive PI3K might be responsible for production of PtdIns(3,4,5)P₃ in response to agonists like ATP, fMLP etc.

Identification of the mechanism by which PI3K activity is activated by cellular agonists which transduce their signals through G protein linked receptors is lacking. It is important to note that the majority of agonists which activate the neutrophil respiratory burst involved in the inflammatory response will bind to G-protein-coupled receptors rather than receptor tyrosine kinases. Thus, the mechanism by which PI3K is regulated in response to these types of chemokines is likely to be different from regulation by growth factors which signal through tyrosine kinases.

Although there is some information concerning the initial events that affect the expression of PI3K, and the products resulting therefrom, much less is known concerning the factors that regulate the pathway from expression to product formation. It will be appreciated that the identification of such factors will have significant medical applications.

The present invention is directed towards resolving, at least in part, this issue by the identification, purification, and cloning of a novel PI3K associated protein.

SUMMARY OF THE INVENTION

A first object of the invention is the description of nucleotides that encode PI3K associated proteins.

A second object of the invention is the description of nucleotides that encode PI3K associated protein(s), which protein(s) bind to the intermediate SH2 domain on the regulatory subunit of p85 of PI3K, and further exhibit a bromodomain.

A third object of the invention is the description of nucleotides that encode PI3K associated protein(s), which protein(s) bind to the intermediate SH2 domain on the regulatory subunit of p85 of PI3K by the associated protein (s) C-terminal amino acids.

A fourth object of the invention is the description of methods for the expression of nucleotides that encode PI3K associated proteins, which proteins exhibit a bromodomain and the purification of the expressed proteins.

A fifth object of the invention is the description of isolated nucleic acid or protein fragments of PI3K associated proteins, respectively.

A sixth object of the invention is to describe host cells transformed with isolated nucleic acid sequences that encodes PI3K associated proteins or fragments thereof.

A seventh object of the invention is to describe vectors that contain isolated nucleic acid sequences that encode PI3K associated proteins or fragments thereof.

A eighth object of the invention is to describe complexes consisting of full length or fragments of PI3K associated proteins and PI3K.

A ninth object of the invention is to describe methods of diagnosing disease using isolated nucleic acid sequences, or fragments thereof, that encode PI3K associated proteins, or fragments thereof.

A tenth object of the invention is to describe an assay for identifying compounds that would have prophalytic or therapeutic applications for the treatment of disease, preferably agonists and antagonists of PI3K regulation, including small molecules, mutant PI3K associated proteins that compete with native PI3K associated proteins for binding to the regulatory subunit of PI3K, antibodies, and nucleotide sequences that can be used to inhibit PI3K associated protein gene expression (e.g., antisense and ribozyme molecules, and gene or regulatory sequence replacement constructs) or to enhance PI3K associated protein gene expression (e.g., expression constructs that place the PI3K associated protein gene under the control of a strong promoter system), and transgenic cells and animals that express a PI3K associated protein transgene or "knock-outs" that do not express PI3K associated protein. Such diseases would include those involving unregulated cell growth, including restinosis, and cancer.

These and other objects of the present invention will become apparent to one of ordinary skill in the art upon reading the description of the various aspects of the invention in the following specification. The foregoing and other aspects of the present invention are explained in greater detail in the drawings, detailed description, and examples set forth below.

DEFINITIONS

As used herein, the following terms, whether used in the singular or plural, will have the meanings indicated:

G protein-regulated PI3K: refers to a PI3K enzyme whose activity is stimulated by activated trimeric G proteins such as Gβγ subunits and/or G α-GTP subunits.

p85: means the regulatory subunit of PI3K, also known as the adapter subunit. p85 includes molecules that are homologous to p85 or which bind to p110, tyrosine kinase receptor-regulated PI3K, at the intermediate SH2 domain (the region between the two SH2 domains and consisting of amino acids 434 to 599, according to the amino acid position numbering of Klippel et al., Mol. Cell. Biol, vol. 13: 5560 (1993)), and stimulate PI3K catalytic activity.

p85 nucleotides or coding sequences: means nucleotide sequences encoding the p85 regulatory subunit protein, polypeptide or peptide fragments of p85, or p85 fusion proteins. p85 nucleotide sequences encompass DNA, including genomic DNA (e.g. the p85 gene) or cDNA, or RNA. Human p85 has been cloned as described by Skolnik et al., Cell, vol. 65: pages 83–90 (1991)

p110: means the catalytic subunit of PI3K. Functional equivalents of p110 refer to a PI3K catalytic subunit protein which binds to the p85 regulatory subunit with high affinity in vivo or in vitro. Other functional equivalents of p110 are homologous catalytic subunits of PI3K.

p110 nucleotides or coding sequences: means nucleotide sequences encoding the p110 catalytic subunit protein, polypeptide or peptide fragments of p110 protein, or p110 fusion proteins. p110 nucleotide sequences encompass DNA, including genomic DNA (e.g. the p110 gene) or cDNA, or RNA. Human p110 has been cloned as described by Hu et al. Mol. Cell. Biol., vol. 13 (12) pages 7677–7688

DESCRIPTION OF THE TABLES

Table 1 shows the plasmid constructs containing certain regions of PIKAP and p85 that were used to perform two-hybrid assays.

Table 2 shows the two-hybrid screening results with specific constructs of PIKAP and p85 which establish that binding of PIKAP to p85 is to the inter SH2 domain of p85, and through the c-terminal end of PIKAP.

DETAILED DESCRIPTION OF THE INVENTION

All publications and patent applications mentioned in this specification are herein incorporated by reference to the same extent as if each individual publication or patent application was specifically and individually indicated to be incorporated by reference.

The present invention relates to the identification, purification, and cloning of PI3K associated protein(s) which protein(s) bind to the inter SH2 domain (the region between the two SH2 domains) on the regulatory subunit of p85 of PI3K by the associated protein(s) C-terminal amino acids, and preferably through no more than the last 74 C-terminal amino acids. Such proteins also exhibit a bromodomain.

PI3K are enzymes which phosphorylate phosphatidyl inositols at the 3d position to generate the intracellular signaling molecule PtdIns(3,4,5)P$_3$. It has been shown that PI3K's are induced in a variety of cell types upon stimulation of tyrosine kinase receptors.

Reported herein is the discovery that certain proteins associate with PI3K and affect its activity. Thus, the invention encompasses such proteins, termed PI3K Associated Proteins (PIKAP), or peptides, the use of PIKAP nucleotides, as well as antibodies to PIKAP which can, for example, act as PIKAP agonists or antagonists, antagonists that inhibit PI3K activity or expression, or agonists that activate PI3K activity in the treatment of PI3K cell activation disorders, including, but not limited to diseases associated with uncontrolled cell growth (cell growth disorders), preferably restinosis and cancer.

Further, the invention encompasses the use of PI3K Associated Protein (PIKAP) nucleotides, proteins and peptides, as well as antibodies to PIKAP in the diagnosis of PI3K cell activation disorders. The diagnosis of an abnormality PI3K Associated Protein (PIKAP) nucleotides, proteins or peptides in a patient, or an abnormality in the activated PI3K signal transduction pathway, will also assist in devising a proper treatment or therapeutic regimen.

In particular, the invention described in the sections below encompasses PIKAP, polypeptides or peptides that display functional domains that interact with the regulatory subunit of PI3K, preferably p85, or the same that is mutated, truncated or deleted (e.g. a regulatory subunit of PI3K or a functional domain of the regulatory subunit, fused to an unrelated protein or peptide such as an epitope tag, i.e., the myc epitope), nucleotide sequences encoding such products, and host cell expression systems that can produce such regulatory subunit products.

The invention also encompasses antibodies and anti-idiotypic antibodies (including Fab fragments), antagonists and agonists of PIKAP, as well as compounds or nucleotide constructs that inhibit expression of nucleotide sequences that encode PIKAP (transcription factor inhibitors, antisense and ribozyme molecules, or gene or regulatory sequence replacement constructs), or promote expression of PIKAP (e.g., expression constructs in which PIKAP coding sequences are operatively associated with expression control elements such as promoters, promoter/enhancers, etc.). The invention also relates to host cells and animals genetically engineered to express the human PIKAP (or mutants thereof) or to inhibit or "knock-out" expression of the animal's endogenous PIKAP.

PIKAP, peptides, fusion proteins, nucleotide sequences, antibodies, antagonists and agonists can be useful for the detection of mutant PIKAP or inappropriately expressed PIKAP for the diagnosis of disease, preferably immune disorders. The above compositions alone or in combination with host cell expression systems, antibodies, antagonists, agonists and genetically engineered cells and animals can be used for screening for drugs effective in the treatment of such disease. The use of engineered host cells and/or animals may offer an advantage in that such systems allow not only for the identification of compounds that bind to the PIKAP, but can also identify compounds that affect the signal transduced by the PI3K, specifically, production of the intracellular signaling molecule PtdIns(3,4,5)P$_3$.

Finally, PIKAP, fusion protein products, antibodies and anti-idiotypic antibodies (including Fab fragments), antagonists or agonists (including compounds that modulate signal transduction which may act on downstream targets in the PI3K signal transduction pathway can be used for therapy of such diseases. For example, nucleotide constructs encoding functional PIKAP, mutant PIKAP, as well as antisense and ribozyme molecules can be used in "gene therapy" approaches for the modulation of PIKAP expression and/or activity in the treatment of disease.

Numerous methods are available for isolating nucleotide sequences that encodes PIKAP, and preferably a cDNA sequence. One method takes advantage of the association of PIKAP with PI3K, and is generally used to identify protein-protein interactions. It is the two-hybrid system, and it is described herein in detail for illustration only and not by way of limitation. This system has been described in U. S. Pat. No. 5,283,173 and by Chien et al., 1991, Proc. Natl. Acad. Sci. USA, 88:9578–9582, and is commercially available from Clontech (Palo Alto, Calif.). Briefly, utilizing such a system, plasmids are constructed that encode two hybrid proteins: one plasmid consists of nucleotides encoding the DNA-binding domain of a transcription activator protein fused to a PI3K p85 nucleotide sequence encoding p85, or p85 peptide or fusion protein, and the other plasmid consists of nucleotides encoding the transcription activator protein's activation domain fused to a cDNA encoding an unknown protein, or in the instant case PIKAP, which has been recombined into this plasmid as a part of the cDNA library. The DNA-binding domain fusion plasmid and the cDNA library are transformed into a strain of yeast *Saccharomyces cerevisiae* that contains a reporter gene (e.g., HIS3 or lacZ) with a regulatory region that contains the transcription activator's binding site. Either hybrid protein alone cannot activate transcription of the reporter gene; the DNA-binding domain hybrid cannot because it does not provide activation function, and the activation domain hybrid cannot because it cannot localize to the activator's binding sites. Interaction of the two hybrid proteins reconstitutes the functional activator protein and results in transcriptional activation of the reporter gene, which is detected by an assay for the reporter gene product.

The two-hybrid system or related methodology may be used to screen activation domain libraries for proteins that interact with the "bait" gene product. By way of example, and not by way of limitation, preferably p85 is used as the bait gene product. Total genomic or cDNA sequences are fused to the DNA encoding an activation domain. This library and the plasmid encoding a hybrid of a bait p85 gene product fused to the DNA-binding domain are cotransformed into a yeast reporter strain, and the resulting tranformants are screened for those that have transcriptionally activated reporter gene. For example, and not by way of limitation, a bait p85 gene sequence can be cloned into a vector such that it is translationally fused to the DNA encoding the DNA-binding domain of the GAL4 protein. These colonies are purified and the library plasmids responsible for reporter gene transcription are isolated. DNA sequencing is then used to determine the nucleotide sequence of the clones which, in turn, reveals the identity of the protein sequences encoded by the library plasmids.

A cDNA library of the cell line from which proteins that interact with bait p85 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait p85 gene-GAL4 fusion plasmid into a yeast strain which contains a lacZ gene driven by a promoter which contains GAL4 activation sequence. A cDNA encoded protein, fused to GAL4 transcriptional activation domain, that interacts with bait p85 gene product will reconstitute an active GAL4 protein and thereby drive expression off the HIS3 gene. Colonies which express HIS3 can be detected by their growth on petri dishes containing semi-solid agar based media lacking histidine. The cDNA can then be purified from these strains, and used to produce and isolate the p85 gene-interacting protein using techniques routinely practiced in the art.

Using the above described two-hybrid technique a PI3 Kinase associated protein (PIKAP) was identified, and shown to have certain unique properties, including a bromodomain. Briefly, the cDNA encoding human PI3K p85 (see Skolnik et al., Cell 65:83–90) was digested with Asp 718 and PstI and the full length p85 sequence was fused to the GAL4 binding domain in the SmaI-PstI sites of pGBT8 plasmid, which is the pMA424 plasmid of Chien et al. as described in Proc. Natl. Acad. Sci. vol. 88: pages 9578–9582 (1991), modified by the insertion of the sequence 5'-CCGGGGATCCCCATGGCTAGCCATATG-3' (SEQ ID NO. 3) between the EcoRI and SalI unique sites. This was transformed into the yeast strain YGH1, and the YGH1 strain carrying the plasmid GAL4-p85 was evaluated for its intrinsic ability to activate the two reporters-growth in histidine minus media and β-galactosidase activity. The YGH1 strain carrying the plasmid GAL4-p85 was subsequently transformed with a HeLa cell cDNA library fused to the GAL4 activation domain in the pGAD plasmid (Chien et al., Proc. Natl. Acad. Sci. vol. 88: pages 9578–9582 (1991). When a cDNA encodes a PIKAP that interacts with the p85, the YGH1 strain is expected to grow in the absence of histidine and produce β-galactosidase.

One screening was done with full length p85 fused to Gal 4 DNA binding domain (Asp 718-PstI, amino acids (AA) 6 to the end of p85). $2 \times 10^5$ transformants were screened. 14 clones conferred ability to grow in the absence of histidine and to produce β-galactosidase. The plasmids recovered from these yeast strains were used to re-transform the original YGH1 GAL4-p85 strain. Again, all the plasmids conferred the ability to grow in the absence of histidine and to produce β-galactosidase. Upon subsequent screening; 12 of the 14 were found to have cDNAs that encode PIKAP that clearly bound to p85. The cDNAs encode various NH2 terminal truncations; the largest had 1232 base pairs and exhibited an open reading frame of 943 bp. Northern blot analysis on human tissue mRNAs using a radio labeled PCR probe corresponding to bp 1493–1683 of the full length sequence revealed a mRNA of about 2.4 Kb.

Thus, the missing 5' sequences of PIKAP were isolated from a human pancreatic cDNA library (Stratagene, Corp.) using sequences present in PIKAP, and these are bp 1160–1460. A clone was isolated containing 2307 base pairs plus a polyadenosine tail of 20 adenosines. It exhibits a start codon at base pair 162, and an open reading frame of 1767 base pairs, and thus encodes a protein with 589 amino acids.

The cDNA sequence (SEQ. ID. No. 1) and deduced amino acid sequence (SEQ. ID. No. 2) of human PIKAP are shown in the Sequence Listing, respectively. The calculated molecular weight is 69 kDa. Particularly noteworthy is the presence of a bromodomain.

The nucleotide sequence encoding the last 74 amino acids of PIKAP is believed to be sufficient to bind p85. Other domains of PIKAP are described by amino acid residues from about 151 to 313 define a bromodomain (Haynes et al., Nucleic Acids Research, Vol. 20, No. 10, p2603) Bromodomains may be involved in protein protein interactions.

The PIKAP nucleotide sequences of the invention include: (a) the DNA sequence shown in FIG. 1 or contained in the cDNA clone PIKAP as deposited with the American Type Culture Collection (ATCC) under accession number 98189; (b) nucleotide sequence that encodes the amino acid sequence shown in FIG. 2, or the PIKAP amino acid sequence encoded by the cDNA clone PIKAP as deposited with the ATCC; (c) any nucleotide sequence that hybridizes to the complement of the DNA sequence shown in FIG. 1 or contained in the cDNA clone pPIKAP as deposited with the ATCC under highly stringent conditions, e.g., hybridization to filter-bound DNA in 0.5 M NaHPO$_4$, 7% sodium dodecyl sulfate (SDS), 1 mM EDTA at 65% C, and washing in 0.1×SSC/0.1% SDS at 68% C (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and (d) any nucleotide sequence that hybridizes to the complement of the DNA sequences that encode the amino acid sequence shown in FIG. 1 or contained in the cDNA clone of the pPIKAP as deposited with the ATCC under less stringent conditions, such as moderately stringent conditions, e.g., washing in 0.2×SSC/0.1% SDS at 42% C (Ausubel et al., 1989, supra), yet which still encodes a functionally equivalent PIKAP gene product. Functional equivalents of the PIKAP include naturally occurring PIKAP present in other species, and mutant PIKAPs whether naturally occurring or engineered which retain at least some of the functional activities of PIKAP (i.e., binding to the p85. The invention also includes degenerate variants of sequences (a) through (d).

The invention also includes nucleic acid molecules, preferably DNA molecules, that hybridize to, and are therefore the complements of, the nucleotide sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37% C (for 14-base oligos), 48% C (for 17-base oligos), 55% C (for 20-base oligos), and 60% C (for 23-base oligos). These nucleic acid molecules may encode or act as PIKAP antisense molecules, useful, for example, in PIKAP gene regulation (for and/or as antisense primers in amplification reactions of PIKAP gene nucleic acid sequences). With respect to PIKAP gene regulation, such techniques can be used to regulate, for example, inflammatory immune responses. Further, such sequences may be used as part of ribozyme and/or triple helix sequences, also useful for PIKAP gene regulation. Still further, such molecules may be used as components of diagnostic methods whereby, for example, the presence of a particular PIKAP allele responsible for causing an inflammatory response, such as arthritis, may be detected.

In addition to the PIKAP nucleotide sequences described above, full length PIKAP cDNA or gene sequences present in the same species and/or homologs of the PIKAP gene present in other species can be identified and readily isolated, without undue experimentation, by molecular biological techniques well known in the art. Therefore, homologs of PIKAP can be readily identified and isolated from a cDNA library.

The identification of homologs of PIKAP in related species can be useful for developing animal model systems more closely related to humans for purposes of drug discovery. For example, expression libraries of cDNAs synthesized from neutrophil mRNA derived from the organism of interest can be screened using labeled catalytic subunit derived from that species, e.g., a p110, or p110 catalytic subunit fusion protein. Alternatively, such cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more domains of the PIKAP gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15–30 base pairs of the PIKAP nucleotide sequence, as shown in FIG. 1. The hybridization washing conditions used should be of a lower stringency when the cDNA library is derived from an organism different from the type of organism from which the labeled sequence was derived.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled PIKAP nucleotide probe may be used to screen a genomic library derived from the organism of interest, again, using appropriately stringent conditions. The identification and characterization of human genomic clones is helpful for designing diagnostic tests and clinical protocols for treating cell growth disorders in human patients. For example, sequences derived from regions adjacent to the intron/exon boundaries of the human gene can be used to design primers for use in amplification assays to detect mutations within the exons, introns, splice sites (e.g. splice acceptor and/or donor sites), etc., that can be used in diagnostics.

Further, a PIKAP gene homolog may be isolated from nucleic acid of the organism of interest by performing PCR using two degenerate oligonucleotide primer pools designed on the basis of amino acid sequences within the PIKAP gene product disclosed herein. The template for the reaction may be cDNA obtained by reverse transcription of mRNA prepared from, for example, human or non-human cell lines or cell types, such as neutrophils, known or suspected to express a PIKAP gene allele.

The PCR product may be subcloned and sequenced to ensure that the amplified sequences represent the sequences of a PIKAP gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular source (i.e., one known, or suspected, to express the PIKAP gene, such as, for example, neutrophils or other types of leukocytes). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

The PIKAP gene sequences may additionally be used to isolate mutant PIKAP gene alleles. Such mutant alleles may be isolated from individuals either known or proposed to have a genotype which contributes to the symptoms of hematopoietic lineage cell activation disorders such as inflammation. Mutant alleles and mutant allele products may then be utilized in the therapeutic and diagnostic systems described below. Additionally, such PIKAP gene sequences can be used to detect PIKAP gene regulatory (e.g., promoter or promotor/enhancer) defects.

A cDNA of a mutant PIKAP gene may be isolated, for example, by using PCR, a technique which is well known to those of skill in the art. In this case, the first cDNA strand may be synthesized by hybridizing an oligo-dT oligonucleotide to mRNA isolated from cells known or suspected to be expressed in an individual putatively carrying the mutant PIKAP allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant PIKAP allele to that of the normal PIKAP allele, the mutation(s) responsible for the loss or alteration of function of the mutant PIKAP gene product can be ascertained.

Alternatively, a genomic library can be constructed using DNA obtained from an individual suspected of or known to carry the mutant PIKAP allele, or a cDNA library can be constructed using RNA from a cell type known, or suspected, to express the mutant PIKAP allele. The normal PIKAP gene or any suitable fragment thereof may then be labeled and used as a probe to identify the corresponding mutant PIKAP allele in such libraries. Clones containing the mutant PIKAP gene sequences may then be purified and subjected to sequence analysis according to methods well known to those of skill in the art.

Additionally, an expression library can be constructed utilizing cDNA synthesized from, for example, RNA isolated from a cell type known, or suspected, to express a mutant PIKAP allele in an individual suspected of or known to carry such a mutant allele. In this manner, gene products made by the putatively mutant cell type may be expressed and screened using standard antibody screening techniques in conjunction with antibodies raised against the normal PIKAP gene product, as described, below (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled fusion proteins. In cases where a PIKAP mutation results in an expressed gene product with altered function e.g., as a result of a missense or a frameshift mutation), a polyclonal set of antibodies to PIKAP are likely to cross-react with the mutant PIKAP gene product. Library clones detected via their reaction with such labeled antibodies can be purified and subjected to sequence analysis according to methods well known to those of skill in the art.

The invention also encompasses nucleotide sequences that encode mutant PIKAPs, peptide fragments of the PIKAP, truncated PIKAPs, and PIKAP fusion proteins. These include, but are not limited to nucleotide sequences encoding mutant PIKAPs described below; polypeptides or peptides corresponding to the catalytic binding, or Gβ subunit binding domains of the PIKAP or portions of these domains; truncated PIKAPs in which one or two of the domains is deleted, or a truncated, nonfunctional PIKAP. Nucleotides encoding fusion proteins may include but are not limited to full length PIKAP, truncated PIKAP or peptide fragments of PIKAP fused to an unrelated protein or peptide, such as for example, an epitope tag which aids in purification or detection of the resulting fusion protein; or an enzyme, fluorescent protein, luminescent protein which can be used as a marker.

The invention also encompasses (a) DNA vectors that contain any of the foregoing PIKAP coding sequences and/or their complements (i.e., antisense); (b) DNA expression vectors that contain any of the foregoing PIKAP coding sequences operatively associated with a regulatory element that directs the expression of the coding sequences; and (c) genetically engineered host cells that contain any of the foregoing PIKAP coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the baculovirus promoter, cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast mating factors.

PIKAP

PIKAP can be prepared for a variety of uses, including but not limited to the generation of antibodies, as reagents in diagnostic assays, the identification of other cellular gene products involved in the regulation of cell growth disorders, and as reagents in assays for screening for compounds that can be used in the treatment of such disorders.

The PIKAP amino acid sequences of the invention include the amino acid sequence shown in FIG. 2 (SEQ. ID. No:2), or the amino acid sequence encoded by the cDNA clone PIKAP, as deposited with the ATCC. Further, PIKAPs of other species are encompassed by the invention. In fact, any PIKAP protein encoded by the PIKAP nucleotide sequences described above, are within the scope of the invention.

The invention also encompasses proteins that are functionally equivalent to the PIKAP encoded by the nucleotide sequences described above, as judged by any of a number of criteria, including but not limited to the ability to bind p85, the ability to affect PI3K activity. Such functionally equivalent PIKAP proteins include but are not limited to additions or substitutions of amino acid residues within the amino acid sequence encoded by the PIKAP nucleotide sequences described, above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to PIKAP DNA (using random mutagenesis techniques well known to those skilled in the art) and the resulting mutant PIKAPs tested for activity, site-directed mutations of the PIKAP coding sequence can be engineered (using site-directed mutagenesis techniques well known to those skilled in the art) to generate mutant PIKAPs with increased function, e.g., higher binding affinity for catalytic subunit, and/or greater signaling capacity; or decreased function, e.g., lower binding affinity for catalytic subunit, and/or decreased signal transduction capacity.

For example, porcine PIKAP amino acid sequence may be aligned with that of human PIKAP. Mutant PIKAPs can be engineered so that regions of interspecies identity are maintained, whereas the variable residues are altered, e.g., by deletion or insertion of an amino acid residue(s) or by substitution of one or more different amino acid residues. Conservative alterations at the variable positions can be engineered in order to produce a mutant PIKAP that retains function. Non-conservative changes can be engineered at these variable positions to alter function. Alternatively, where alteration of function is desired, deletion or non-conservative alterations of the conserved regions can be engineered. One of skill in the art may easily test such mutant or deleted PIKAPs for these alterations in function using the teachings presented herein.

Other mutations to the PIKAP coding sequence can be made to generate PIKAPs that are better suited for expression, scale up, etc. in the host cells chosen. For example, the triplet code for each amino acid can be modified to conform more closely to the preferential codon usage of the host cell's translational machinery.

Peptides corresponding to one or more domains (or a portion of a domain) of PIKAP (e.g., the p85 binding, bromodomain), truncated or deleted PIKAPs (e.g., PIKAP in which portions of one or more of the above domains are deleted) as well as fusion proteins in which the full length PIKAP, a PIKAP peptide or truncated PIKAP is fused to an unrelated protein are also within the scope of the invention and can be designed on the basis of the PIKAP nucleotide and PIKAP amino acid sequences disclosed in this section and above. Such fusion proteins include but are not limited to fusions to an epitope tag (such as is exemplified in the Examples below); or fusions to an enzyme, fluorescent protein, or luminescent protein which provide a marker function.

While the PIKAP polypeptides and peptides can be chemically synthesized (e.g., see Creighton, 1983, Proteins: Structures and Molecular Principles, W.H. Freeman & Co., N.Y.), large polypeptides derived from the PIKAP and the full length PIKAP itself may advantageously be produced by recombinant DNA technology using techniques well known in the art for expressing nucleic acid containing PIKAP gene sequences and/or coding sequences. Such methods can be used to construct expression vectors containing the PIKAP nucleotide sequences described above and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding PIKAP nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the PIKAP nucleotide sequences of the invention. Where the PIKAP peptide or polypeptide is a soluble derivative the peptide or polypeptide can be recovered from the culture, i.e., from the host cell in cases where the PIKAP peptide or polypeptide is not secreted, and from the culture media in cases where the PIKAP peptide or polypeptide is secreted by the cells. However, such engineered host cells themselves may be used in situations where it is important not only to retain the structural and functional characteristics of the PIKAP, but to assess biological activity, e.g., in drug screening assays.

The expression systems that may be used for purposes of the invention include but are not limited to microorganisms such as bacteria (e.g., E. coli, B. subtilis) transformed with recombinant bacteriophage DNA, plasmid DNA or cosmid DNA expression vectors containing PIKAP nucleotide sequences; yeast (e.g., Saccharomyces, Pichia) transformed with recombinant yeast expression vectors containing the PIKAP nucleotide sequences; insect cell systems infected with recombinant virus expression vectors (e.g., baculovirus) containing the PIKAP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing PIKAP nucleotide sequences; or mammalian cell systems (e.g., COS, CHO, BHK, 293, 3T3, U937) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the PIKAP gene product being expressed. For example, when a large quantity of such a protein is to be produced, for the generation of pharmaceutical compositions of PIKAP protein or for raising antibodies to the PIKAP protein, for example, vectors which direct the expression of high levels of fusion protein products that are readily purified may be desirable. Such vectors include, but are not limited to, the E. coli expression vector pUR278 (Ruther et al., 1983, EMBO J. 2:1791), in which the PIKAP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). If the inserted sequence encodes a relatively small polypeptide (less than 25 kD), such fusion proteins are generally soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. Alternatively, if the resulting fusion protein is insoluble and forms inclusion bodies in the host cell, the inclusion bodies may be purified and the recombinant protein solubilized using techniques well known to one of skill in the art.

In an insect system, *Autographa californica* nuclear polyhidrosis virus (AcNPV) may be used as a vector to express foreign genes. (E.g., see Smith et al., 1983, J. Virol. 46: 584; Smith, U.S. Pat. No. 4,215,051).

In mammalian host cells, a number of viral-based expression systems may be utilized preferably using a CMV promoter to transiently express recombinant protein in U937 cells or in Cos-7 cells. Alternatively, retroviral vector systems well known in the art may be used to insert the recombinant expression construct into host cells. For example, retroviral vector systems for transducing cells are described in published PCT applications WO 96/09400 and WO 94/29438.

In cases where an adenovirus is used as an expression vector, the PIKAP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the PIKAP gene product in infected hosts. (E.g., See Logan & Shenk, 1984, Proc. Natl. Acad. Sci. USA 81:3655–3659). Specific initiation signals may also be required for efficient translation of inserted PIKAP nucleotide sequences. These signals include the ATG initiation codon and adjacent sequences. In cases where an entire PIKAP gene or cDNA, including its own initiation codon and adjacent sequences, is inserted into the appropriate expression vector, no additional translational control signals may be needed. However, in cases where only a portion of the PIKAP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript may be used. Such mammalian host cells include but are not limited to CHO, VERO, BHK, HeLa, COS, MDCK, 293, 3T3, WI38, and U937 cells.

For long-term, high-yield production of recombinant proteins, stable expression is preferred. For example, cell lines which stably express the PIKAP sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the PIKAP gene product. Such engineered cell lines may be particularly useful in screening and evaluation of compounds that affect the endogenous activity of the PIKAP gene product.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

The PIKAP gene product can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate PIKAP transgenic animals.

Any technique known in the art may be used to introduce the PIKAP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the PIKAP transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the PIKAP gene transgene be integrated into the chromosomal site of the endogenous PIKAP gene, gene targeting is preferred. Briefly, when such a technique is to be utilized, vectors containing some nucleotide sequences homologous to the endogenous PIKAP gene are designed for the purpose of integrating, via homologous recombination with chromosomal sequences, into and disrupting the function of the nucleotide sequence of the endogenous PIKAP gene. In this way, the expression of the endogenous PIKAP gene may also be eliminated by inserting non-functional sequences into the endogenous gene. The transgene may also be selectively introduced into a particular cell type, thus inactivating the endogenous PIKAP gene in only that cell type, by following, for example, the teaching of Gu et al. (Gu et al., 1994, Science 265: 103–106). The regulatory sequences required for such a cell-type specific inactivation will depend upon the particular cell type of interest, and will be apparent to those of skill in the art.

Once transgenic animals have been generated, the expression of the recombinant PIKAP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of cell type samples obtained from the animal, in situ hybridization analysis, and RT-PCR. Samples of PIKAP gene-expressing tissue, may also be evaluated immunocytochemically using antibodies specific for the PIKAP transgene product, as described below.

Diagnosis of Cell Growth Disorders

A variety of methods can be employed for the diagnostic and prognostic evaluation of cell growth disorders, including restinosis and cancer, and for the identification of subjects having a predisposition to such disorders.

Such methods may, for example, utilize reagents such as the PIKAP nucleotide sequences, and PIKAP antibodies, as described above. Specifically, such reagents may be used, for example, for: (1) the detection of the presence of PIKAP gene mutations, or the detection of either over- or under-expression of PIKAP mRNA relative to the non cell growth disorder state; (2) the detection of either an over- or an under-abundance of PIKAP gene product relative to the non-cell growth disorder state; and (3) the detection of perturbations or abnormalities in the signal transduction pathway mediated by PIKAP.

The methods described herein may be performed, for example, by utilizing pre-packaged diagnostic kits comprising at least one specific PIKAP nucleotide sequence or PIKAP antibody reagent described herein, which may be conveniently used, e.g., in clinical settings, to diagnose patients exhibiting cell activation disorder abnormalities.

For the detection of PIKAP, any nucleated cell can be used as a starting source for genomic nucleic acid. For the detection of PIKAP expression, any cell type or tissue in which the PIKAP is expressed may be utilized.

Nucleic acid-based detection techniques are described, below. Peptide detection techniques are also described below.

Detection of the PIKAP Gene and Transcripts

Mutations within the PIKAP gene(s) can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of PIKAP specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described above, under conditions favorable for the specific annealing of these reagents to their complementary sequences within the PIKAP. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled PIKAP nucleic acid reagents is accomplished using standard techniques well known to those in the art. The PIKAP gene sequences to which the nucleic acid reagents have annealed can be compared to the annealing pattern expected from a normal gene sequence in order to determine whether a gene mutation is present.

Alternative diagnostic methods for the detection of PIKAP gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of the PIKAP gene in order to determine whether a gene mutation exists.

Additionally, well-known genotyping techniques can be performed to identify individuals carrying PIKAP gene mutations. Such techniques include, for example, the use of restriction fragment length polymorphisms (RFLPs), which involve sequence variations in one of the recognition sites-for the specific restriction enzyme used.

The level of PIKAP gene expression can also be assayed by detecting and measuring PIKAP transcription. For example, RNA from a cell type or tissue known, or suspected to express the PIKAP gene, such as hematopoietic lineage cells, especially myeloid cells and platelets, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the PIKAP gene. Such analyses may reveal both quantitative and qualitative aspects of the expression pattern of the PIKAP, including activation or inactivation of PIKAP gene expression.

Detection of the PIKAP Gene Products

Antibodies directed against wild type or mutant PIKAP gene products or conserved variants or peptide fragments thereof, which are discussed, above, may also be used as cell growth disorder diagnostics and prognostics, as described herein. Such diagnostic methods, may be used to detect abnormalities in the level of PIKAP gene expression, or abnormalities in the structure and/or temporal, tissue, cellular, or subcellular location of the PIKAP, and may be performed in vivo or in vitro, such as, for example, on biopsy tissue.

The tissue or cell type to be analyzed will generally include those which are known, or suspected, to contain cells express the PIKAP gene, such as, for example, neutrophil cells which have infiltrated an inflamed tissue. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the PIKAP gene.

For example, antibodies, or fragments of antibodies, such as those described above are useful in the present invention to quantitatively or qualitatively detect the presence of PIKAP gene products or conserved variants or peptide fragments thereof. This can be accomplished, for example, by immunofluorescence techniques employing a fluorescently labeled antibody (see below) coupled with light microscopic, flow cytometric, or fluorimetric detection.

The antibodies (or fragments thereof or fusion or conjugated proteins useful in the present invention may, additionally, be employed histologically, as in immunofluorescence, immunoelectron microscopy or non-immuno assays, for in situ detection of PIKAP gene products or conserved variants or peptide fragments thereof, or for p85 binding (in the case of labeled p85 fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the PIKAP gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for PIKAP gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying PIKAP gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled PIKAP antibody or fusion protein. The solid phase support may then be washed with the buffer a second time to remove unbound antibody or fusion protein. The amount of bound label on solid support may then be detected by conventional means.

"Solid phase support or carrier" is intended to encompass any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of PIKAP subunit antibody or fusion protein may be determined according to well known methods. Those skilled in the art will be able to determine operative and optimal assay conditions for each determination by employing routine experimentation.

With respect to antibodies, one of the ways in which the antibody can be detectably labeled is by linking the same to an enzyme and use in an enzyme immunoassay (EIA) (Voller, "The Enzyme Linked Immunosorbent Assay (ELISA)", 1978, Diagnostic Horizons 2:1–7, Microbiological Associates Quarterly Publication, Walkersville, Md.); Voller et al., 1978, J. Clin. Pathol. 31:507–520; Butler, 1981, Meth. Enzymol. 73:482–523; Maggio (ed.), 1980, Enzyme Immunoassay, CRC Press, Boca Raton, Fla.; Ishikawa et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect PIKAP through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Screening Assays for Compounds That Modulate
PI3K Expression or Activity

The following assays are designed to identify compounds that interact with (e.g., bind to) PIKAP or p85, to affect the binding of PIKAP to p85, compounds that interact with (e.g., bind to) intracellular proteins that interact with PIKAP and/or p85, compounds that interfere with the interaction of PIKAP with p85 or with other intracellular proteins involved in PI3K mediated signal transduction, and to compounds which modulate the activity of PIKAP gene (i.e., modulate the level of PIKAP gene expression) or modulate the level of PIKAP. Assays may additionally be utilized which identify compounds which bind to PIKAP gene regulatory sequences (e.g., promoter sequences) and which may modulate PIKAP gene expression. See e.g., Platt, K. A., 1994, J. Biol. Chem. 269:28558–28562, which is incorporated herein by reference in its entirety.

The compounds which may be screened in accordance with the invention include but are not limited to peptides, antibodies and fragments thereof, prostaglandins, lipids and other organic compounds (e.g., terpines, peptidomimetics) that bind to PIKAP or p85 and either mimic the activity triggered by the natural ligand (i.e., agonists) or inhibit the activity triggered by the natural ligand (i.e., antagonists); as well as peptides, antibodies or fragments thereof, and other organic compounds that mimic PIKAP or p85 (or a portion thereof) and bind to and "neutralize" natural ligand.

Such compounds may include, but are not limited to, peptides such as, for example, soluble peptides, including but not limited to members of random peptide libraries (see, e.g., Lam, K. S. et al., 1991, Nature 354:82–84; Houghten, R. et al., 1991, Nature 354:8486), and combinatorial chemistry-derived molecular library peptides made of D- and/or L-configuration amino acids, phosphopeptides (including, but not limited to members of random or partially degenerate, directed phosphopeptide libraries; see, e.g., Songyang, Z. et al., 1993, Cell 72:767–778); antibodies (including, but not limited to, polyclonal, monoclonal, humanized, anti-idiotypic, chimeric or single chain antibodies, and FAb, F(ab.)$_2$ and FAb expression library fragments, and epitope-binding fragments thereof); and small organic or inorganic molecules.

Other compounds which can be screened in accordance with the invention include but are not limited to small organic molecules that are able to gain entry into an appropriate cell (e.g., in the neutrophil) and affect the expression of the PIKAP gene or some other gene involved in the PIKAP signal transduction pathway (e.g., by interacting with the regulatory region or transcription factors involved in gene expression); or such compounds that affect the activity of the PIKAP, e.g., by inhibiting or enhancing the binding of PIKAP to p85 of PI3K or the binding of PIKAP to some other intracellular factor involved in the PIKAP signal transduction pathway.

Computer modeling and searching technologies permit identification of compounds, or the improvement of already identified compounds, that can modulate PIKAP or p85 expression or activity. Having identified such a compound or composition, the active sites or regions are identified. Such active sites might typically be the binding partner sites, such as, for example, the interaction domains of the p85 with PIKAP itself. Keep in mind that it is shown in the instant patent application that PIKAP and p85 bind to p110 at the same region. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential PIKAP modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of PIKAP that interact with p85, and related transduction and transcription factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp.189–193 (Alan R. Liss, Inc. 1989); Lewis and Dean, 1989, Proc. R. Soc. Lond. 236:125–140 and 141–162; and, with respect to a model receptor for nucleic acid components, Askew et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elaborating the biological function of the PIKAP gene product, and for ameliorating cell growth disorders. Assays for testing the effectiveness of compounds, identified by techniques described herein are discussed below.

In vitro Screening Assays for Compounds That Bind to PIKAP

In vitro systems may be designed to identify compounds capable of interacting with (e.g., binding to) PIKAP and p85. Compounds identified may be useful, for example, in modulating the activity of wild type and/or mutant PIKAP gene products; may be utilized in screens for identifying compounds that disrupt normal PIKAP/p85 interactions; or may in themselves disrupt such interactions.

The principle of the assays used to identify compounds that bind to the PIKAP involves preparing a reaction mixture of the PIKAP and the test compound under conditions and for a time sufficient to allow the two components to interact and bind, thus forming a complex which can be removed and/or detected in the reaction mixture. The PIKAP species used can vary depending upon the goal of the screening assay. For example, where agonists of the natural ligand are sought, the full length PIKAP, or a fusion protein containing the PIKAP fused to a protein or polypeptide that affords advantages in the assay system (e.g., labeling, isolation of the resulting complex, etc.) can be utilized.

The screening assays can be conducted in a variety of ways. For example, one method to conduct such an assay would involve anchoring the PIKAP protein, polypeptide, peptide or fusion protein or the test substance onto a solid phase and detecting PIKAP/test compound complexes anchored on the solid phase at the end of the reaction. In one embodiment of such a method, the PIKAP reactant may be anchored onto a solid surface, and the test compound, which is not anchored, may be labeled, either directly or indirectly. In another embodiment of the method, a PIKAP protein anchored on the solid phase is complexed with labeled p85. Then, a test compound could be assayed for its ability to disrupt the association of the PIKAP/p85 complex.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for PIKAP protein, polypeptide, peptide or fusion protein, or the p85 protein or fusion protein, or the test compound to anchor any complexes formed in solution, and a labeled antibody specific for the other component of the possible complex to detect anchored complexes.

Assays for Intracellular Proteins That Interact With PIKAP

Methods suitable for detecting protein-protein interactions may be employed for identifying intracellular proteins that interact with PIKAP and/or p85. These methods may also be applied to determine the site(s) of interaction of PIKAP with p85. Among the traditional methods which may be employed are co-immunoprecipitation, crosslinking and co-purification through gradients or chromatographic columns of cell lysates or proteins obtained from cell lysates and the PIKAP to identify proteins in the lysate that interact with the PIKAP. For these assays, the PIKAP component used can be a full length PIKAP, or a truncated peptide. Similarly, the component may be p85 and PIKAP, or a complex of PIKAP with p110 and p85. Once isolated, such an intracellular protein can be identified and can, in turn, be used, in conjunction with standard techniques, to identify proteins with which it interacts. The amino acid sequence of an intracellular protein which interacts with the PIKAP can be ascertained using techniques well known to those of skill in the art, such as via the Edman degradation technique. (See, e.g., Creighton, 1983, "Proteins: Structures and Molecular Principles", W.H. Freeman & Co., N.Y., pp.34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of genes which encode the intracellular proteins interacting with PIKAP. These methods include, for example, probing expression, libraries, in a manner similar to the well known technique of antibody probing of gt11 libraries, using labeled PIKAP protein, or a PIKAP polypeptide, peptide or fusion protein, e.g., a PIKAP polypeptide or PIKAP domain fused to a marker (e.g., an enzyme, fluor, luminescent protein, or dye), or an Ig-Fc domain.

One method which detects protein interactions in vivo, the two-hybrid system, is described above in detail for illustration only and not by way of limitation. One version of this system has been described (Chien et al., 1991, Proc. Natl. Acad. Sci. USA, 88:9578–9582) and is commercially available from Clontech (Palo Alto, Calif.). Using this method with specific PIKAP and p85 constructs it was shown that PIKAP binds to p85 at the intermediate SH2 domain. The following constructs were generated and tested in the two-hybrid assay. Table 1 shows the construction strategy for the various p85 or PIKAP constructs that were tested.

Table 1

Plasmid Constructions p85 full length: Asp 718 (bp56) filled in with Klenow-PstI (bp2315) of human p85α into SmaI-PstI of the GBT8 vector.

p85 SH3 domain: Asp 178 (bp56) filled in with Klenow-XhoII (bp390) of human p85α into SmaI-BamHI of the GBT8 vector.

p85 Bcr homology domain: XhoII (bp 390) filled in with Klenow-XhoI (bp 1055) of human p85α into BamHI filled in with Klenow-SalI of the GBT8 vector.

p85 SH2 domains and inter SH2 domain: ScaI (bp 830)-PstI (bp2315) of human p85α into SmaI-PstI of the GBT8 vector.

p85 N-terminal SH2 and inter SH2 domain: p85 SH2 domains and inter SH2 domain construct cut with RcaI (bp1896) and StuI (bp2263), filled in with Klenow and religated without this RcaI-StuI fragment.

p85 C-terminal SH2 domain: RcaI (bp 1896) filled in with Klenow-StuI(bp2263) of human p85α into BamHI filled in with Klenow of the GBT8 vector.

p85 inter SH2 domain:DpnI (bp1343)-RcaI (bp1896) filled in with Klenow of the human p85α into SmaI of the GBT8 vector.

PIKAP AA 277-589: original isolate from two hybrid screening: EcoRI linker (5'GAATCGGCACGAG3') fused to bp989 of submitted PIKAP sequence to bp 2219 in submitted sequence fused to XhoI linker into EcoRI-XhoI of the GADGH vector.

PIKAP AA 277-360: EcoRI linker fused to bp989 (see above)-BamHI (bp1232) into EcoRI-BamHI of the GADGH vector.

PIKAP AA 361-516: BamHI (bp1232)-ScaI (bp1703) into BamHI-SmaI of the GADGH vector.

PIKAP AA517-589: ScaI (bp 1703)-EcoRV (bp1974) into ClaI filled in with Klenow of the GADGH vector.

Table 2 shows the results of performing the two-hybrid assay using the above constructs. It is apparent that the three constructs that have the intermediate SH2 domain deleted do not bind any of the PIKAP constructs. That is: p85 constructs containing only the sh3 domain, aa 6-117, or the Bcr homology domain, aa 118-340, or the c-terminal sh2 domain, do not exhibit binding to any of the PIKAP constructs. In comparison, p85 constructs that contain the inter sh2 domains, including p85 full length (aa 6-727), or sh2 and inter sh2 domains (aa 263-727) or N-terminal sh2 and inter sh2 domains (aa 263-620), or just the inter sh2 domain (aa 435-620), do bind to PIKAP but to only those PIKAP constructs that display the last 74 amino acids of the c-terminal end of the molecule.

It is note worthy that PIKAP binds to the inter-SH2 region of p85 as does p110. See Klippel et al., Mol. Cell. Biol., 14: pages 2675–2685 (1994). Thus, PIKAP may have a regulatory role on the catalytic activity of p110 by competing for binding with p85 to the inter sh2 domain on p85.

TABLE 2

Binding of PIKAP to Inter SH2 of p85

| | PIKAP AA 277–589 | PIKAP AA 277–360 | PIKAP AA 361–516 | PIKAP AA 517–589 |
|---|---|---|---|---|
| p85 full length (AA 6–727) | +++ | – | – | +++ |
| p85 SH3 domain (AA 6–117) | – | | | |
| p85 Bcr homology domain (AA 118–340) | – | | | |
| p85 SH2 domains and inter SH2 domain (AA 263–727) | +++ | – | – | +++ |
| p85 N-terminal SH2 and inter SH2 domain (AA 263–620) | +++ | – | – | +++ |
| p85 C-terminal SH2 domain (AA 620–727) | – | | | |
| p85 inter SH2 domain (AA 435–620) | +++ | – | – | +++ |

Restoration or Increase in PIKAP Expression or Activity to Promote Control of Cell Growth With respect to an increase in the level of normal PIKAP gene expression and/or PIKAP gene product activity, PIKAP nucleic acid sequences can be utilized for the treatment of cell growth disorders, including restinosis and cancer. Where the cause of the cell growth disorders is a defective PIKAP, treatment can be administered, for example, in the form of gene replacement therapy. Specifically, one or more copies of a normal PIKAP gene or a portion of the PIKAP gene that directs the production of a PIKAP gene product exhibiting normal function, may be inserted into the appropriate cells within a patient or animal subject, using vectors which include, but are not limited to adenovirus, adeno-associated virus, retrovirus and herpes virus vectors, in addition to other particles that introduce DNA into cells, such as liposomes.

Because the PIKAP gene is expressed in most cells such gene replacement therapy techniques should be capable of delivering PIKAP gene sequences to these cell types within patients. Alternatively, targeted homologous recombination can be utilized to correct the defective endogenous PIKAP gene in the appropriate cell type; e.g., bone marrow cells or neutrophils and/or other leukocytes.

Finally, compounds identified in the assays described above that stimulate, enhance, or modify the signal transduced by activated PIKAP, e.g., by activating downstream signaling proteins in the PIKAP cascade and thereby by passing the defective PIKAP, can be used to achieve immune system stimulation. The formulation and mode of administration will depend upon the physico-chemical properties of the compound.

Pharmaceutical Preparations

The compounds that are determined to affect PIKAP gene expression or PIKAP activity, or the interaction of PIKAP with any of its binding partners including but not limited to p85, can be administered to a patient at therapeutically effective doses to treat or ameliorate hematopoietic cell growth disorders, including restinosis, and cancer. A therapeutically effective dose refers to that amount of the compound sufficient to result in amelioration of symptoms of such disorders.

Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulations and use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The following examples are presented to illustrate the present invention and to assist one of ordinary skill in making and using the same. The examples are not intended in any way to otherwise limit the scope of the disclosure or the protection granted by Letters patent hereon.

DEPOSIT OF CLONES

The following microorganisms or clones were deposited with the American Type Culture Collection (ATCC), Rockville, Md., on the dates indicated and were assigned the indicated accession number:

| Clone | Access No. | Date of Deposit |
| --- | --- | --- |
| PIKAP | 98189 | Sep. 30, 1996 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated phosphatidylinositol-3'kinase associated protein comprising the polypeptide of SEQ ID NO: 2 wherein the C-terminal amino acids of said phosphatidylinositol-3'kinase associated protein bind to the intermediate src homology 2 (SH2) domain of the regulatory subunit of phosphatidylinositol-3'kinase.

2. A chimeric protein comprising the phosphatidylinositol-3'kinase associated protein of claim 1 fused to a heterologous polypeptide.

3. An isolated phosphatidylinositol-3'kinase associated protein comprising an amino acid sequence, wherein said amino acid sequence comprises the C-terminal amino acids of SEQ ID NO: 2 that bind to the intermediate src homology 2 (SH2) domain of the regulatory subunit of phosphatidylinositol-3'kinase, wherein said phosphatidylinositol-3'kinase associated protein is encoded by a polynucleotide which hybridizes under stringent conditions to the polynucleotide of SEQ ID NO: 1, and wherein said stringent conditions comprise hybridization in 0.5 M $NaHPO_4$, 7% sodium dodecyl sulfate, 1 mM EDTA at 65 degrees centigrade, and washing in 0.1×SSC/0.1% SDS at 68 degrees centigrade.

* * * * *